United States Patent [19]

Iwao et al.

[11] 4,241,086

[45] Dec. 23, 1980

[54] METHOD FOR TREATING RHEUMATISM

[75] Inventors: Jun-ichi Iwao, Takarazuka; Tadashi Iso, Tondabayashi, both of Japan

[73] Assignee: Santen Pharmaceutical Co., Ltd., Osaka, Japan

[21] Appl. No.: 82,330

[22] Filed: Oct. 5, 1979

[30] Foreign Application Priority Data

Oct. 11, 1978 [JP] Japan .................................. 53-125537

[51] Int. Cl.$^3$ .......................................... A61K 31/195
[52] U.S. Cl. .................................................. 424/319
[58] Field of Search .................................. 424/300, 305

[56] References Cited

U.S. PATENT DOCUMENTS 4,053,651  10/1977  Ondetti et al. .................. 424/273 R

*Primary Examiner*—Stanley J. Friedman
*Attorney, Agent, or Firm*—Frishauf, Holtz, Goodman & Woodward

[57] ABSTRACT

A method for treating rheumatism and/or arthritis in mammals afflicted therewith by administering an effective amount of N-(2-mercapto-2-methylpropanoyl)-L-cysteine or a pharmacologically acceptable salt thereof.

2 Claims, No Drawings

METHOD FOR TREATING RHEUMATISM

BACKGROUND OF THE INVENTION

The present invention provides a method for treatment of rheumatism and arthritis.

Recently, D-penicillamine has received world attention as an antirheumatic. It possesses antirheumatic activity without the anti-inflammatory activity found in conventional steroidal and non-steroidal anti-inflammatory agents. It has now been discovered that N-(2-mercapto-2-methylpropanoyl)-L-cysteine (hereinafter referred to as "said cysteine compound") and pharmacologically acceptable salts thereof are effective as antirheumatic agents. Said cysteine compound is disclosed as being an effective agent for the liquefaction of sputum in Application Ser. No. 771,743 filed Feb. 24, 1977. N-(2-mercaptopropanoyl)-L-cysteine is also disclosed in U.S. Pat. No. 4,053,651 issued Oct. 11, 1977 as an agent for alleviating or reducing angiotensin related hypertension. The disclosures of the said patent application and said patent are incorporated herein.

THE INVENTION

The present invention provides a method for treating rheumatic and/or arthritic diseases in mammals afflicted therewith comprising administering an effective dose of N-(2-mercapto-2-methylpropanoyl)-L-cysteine or a pharmacologically acceptable salt thereof. N-(2-mercapto-2-methylpropanoyl)-L-cysteine has the formula

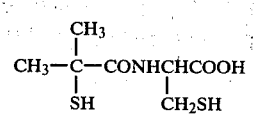

It has a melting point of 139° to 140° and $[\alpha]_D^{25} + 32.3°$ (c=1.0, methanol); and a very low acute toxicity, i.e., $LD_{50}$s are 2285 mg/kg (i.p.) and 989 mg/kg (i.v.) in mice.

The pharmacologically acceptable salts formed by reaction of the said cysteine compound with bases (inorganic and organic) are also useful in the method of the present invention. Such salts include ammonium salts; alkali metal salts, e.g., sodium and potassium salts; alkaline earth metal salts, e.g., calcium and magnesium salts; salts with organic bases, e.g., arginine, lysine, D-glucamine and N-methyl-D-glucamine salts.

Although the tests to date have not established the full extent to which the method of the present invention is effective in treating rheumatism and arthritis, they do establish an effective treatment of said diseases and a substantial alleviation of symptoms which in this field is an important therapeutic effect.

DETAILED DESCRIPTION OF THE INVENTION

Pharmacological Test 1.

Test to establish the inactivating activity of said cysteine compound on the rheumatoid factor.

Most patients suffering from rheumatism exhibit the rheumatoid factor. Inactivation of the rheumatoid factor is considered to be useful in the treatment of rheumatism. The inactivating activity of said cysteine compound was studied in vitro using the glass plate method of Latex agglutination.

Rheumatoid factor positive serum was agitated with said cysteine compound or D-penicillamine in a glycinesodium chloride buffer solution (pH 8.2) for two hours at 37° C. and the activity of rheumatoid factor in the mixed solution was measured using rheumatoid factor test kits "T.S.S." (made by Tokyo Standard Serum Co., Ltd.).

The results are shown in Table 1. The results establish that the rheumatoid factor-inactivating activity of said cysteine compound is much higher than that of D-penicillamine.

TABLE 1

| | Rheumatoid Factor-inactivating Activity | |
|---|---|---|
| Compound | Molar concentration (M) | Intensity of agglutination |
| Control | | ++ |
| | $10^{-4}$ | ++ |
| Said cysteine compound | $10^{-3}$ | ± |
| | $10^{-2}$ | − |
| D-penicillamine | $10^{-3}$ | ++ |
| | $10^{-2}$ | + |

Pharmacological Test 2.

Test to establish treatment for rat adjuvant arthritis.

Male SD strain rats weighing 200 to 220 g (8 rats in each group) were used for the test. Under light ether anesthesia, the rats were injected subcutaneously with 0.6 mg/0.05 ml of Mycobacterium butylicum suspended in liquid paraffin at the subplantan region of hind paw. From the time when the arthritis scores (ear capules, fore paw, untreated hind paw and tails) reached a definite level 15 to 20 days after the injection, said cysteine compound or D-penicillamine was administered orally once a day for 30 days and the antirheumatic activites of these compounds examined by using arthritis score as an index.

The results are shown in Table 2.

TABLE 2

| | Anti-rheumatic Activity | | |
|---|---|---|---|
| | Dosage | Arthritis Scores* | |
| Compound | (mg/kg/day) | Before Admin. | After Admin. |
| Control | | 9.3 ± 1.0 | 12.6 ± 1.3 |
| Said Cysteine Compound | 1 | 9.4 ± 0.9 | 9.3 ± 1.5 |
| | 10 | 9.5 ± 1.0 | 9.4 ± 1.3 |
| D-penicillamine | 1 | 9.3 ± 1.5 | 9.3 ± 1.5 |
| | 10 | 9.5 ± 1.2 | 9.2 ± 1.7 |

*mean value ± standard error

1. In the ear capules, the score is determined on the basis of number and size of erythema stepwise in the range of 0 to 5. Score 0 denotes a normal (healthy) state.

2. On a fore paw, the score is determined on the basis of successive stage of redness and swelling of joint and the degree of transformation of bone stepwise in the range of 0 to 5. Score 0 denotes a normal state.

3. On an untreated hind paw, the score is determined on the basis of successive stage of redness and swelling of joint stepwise in the range of 0 to 5. Score 0 denotes a normal state.

4. On the tail, the score is determined on the basis of number of nodules stepwise in the range of 0 to 5. Score 0 denotes a normal state.

A full score in connection with the four above-noted areas which are examined, which is the worst possible score is 20. A fully normal state would be 0.

The results set forth in Table 2 establish that said cysteine compound is effective for the treatment of rat adjuvant arthritis.

Judging from the results of these pharmacological tests the compound is useful as an antirheumatic.

The usual adult dosage is in the range of from 0.2 to 20 mg per kg a day; said cysteine compound can be administered orally or by injection, i.e., subcutaneous or intravenous.

Said cysteine compound may be processed as a medicinal composition for oral administration, into tablet, powder or encapsulated form so that it is easily absorbed from gastrointestinal tracts as determined for convenience or because one of these forms is preferred. The medicinal composition can contain a binding agent such as gelatin, sorbitol, polyvinyl pyrrolidone; a forming agent such as lactose, starch, calcium phosphate; a lubricating agent such as magnesium stearate, talc; and a collapsing agent such as carboxymethyl cellulose calcium. The composition may be processed into an aqueous solution of said cysteine compound alone or its salts such as sodium salt for the use of injection.

The following formulations are illustrative:

| (1) For oral administration | | |
|---|---|---|
| (a) | Tablet form | |
| | said cysteine compound | 100mg |
| | ethyl cellulose | 50mg |
| | crystalline cellulose | 80mg |
| | carboxymethyl cellulose | 7mg |
| | magnesium stearate | 3mg |
| | Total | 240mg |

Tablet may be (and usually is) coated with a filmcoating. It additionally may be coated with a sugar-coating.

| (b) | Granular form | |
|---|---|---|
| | said cysteine compound | 100mg |
| | polyvinyl pyrrolidone | 25mg |
| | lactose | 365mg |
| | talc | 10mg |
| | Total | 500mg |
| (c) | Powder form | |
| | said cysteine compound | 100mg |
| | lactose | 500mg |
| | starch | 370mg |
| | colloidal silica | 30mg |
| | Total | 1000mg |
| (d) | Encapsulated form | |
| | said cysteine compound | 100mg |
| | lactose | 32mg |
| | crystalline cellulose | 56mg |
| | colloidal silica | 2mg |
| | Total | 190mg |

(2) Injection form 250 mg of said cysteine compound in the form of the sodium salt are contained in 5 ml of an aqueous solution having a pH 6.5–7.0.

We claim:

1. A method for treating rheumatism and arthritis in a mammal afflicted with at least one of the said conditions comprising administering to said mammal an effective dose of N-(2-mercapto-2-methylpropanoyl)-L-cysteine or a pharmacologically acceptable salt thereof.

2. The method of claim 1 wherein the dose is between 0.2 and 20 mg per kg a day.

* * * * *